US008642288B2

United States Patent
Leshansky et al.

(10) Patent No.: US 8,642,288 B2
(45) Date of Patent: Feb. 4, 2014

(54) METHODS FOR VISCOELASTIC FOCUSING OF PARTICLES

(75) Inventors: Alexander Leshansky, Haifa (IL); Avishay Bransky, Tivon (IL); Korin Natanel, Beer-sheva (IL)

(73) Assignee: Technion Research & Development Foundation Ltd., Haifa (IL)

( * ) Notice: Subject to any disclaimer, the term of this patent is extended or adjusted under 35 U.S.C. 154(b) by 467 days.

(21) Appl. No.: 12/663,492

(22) PCT Filed: Jun. 5, 2008

(86) PCT No.: PCT/IL2008/000772
§ 371 (c)(1),
(2), (4) Date: Feb. 2, 2010

(87) PCT Pub. No.: WO2008/149365
PCT Pub. Date: Dec. 11, 2008

(65) Prior Publication Data
US 2010/0178666 A1 Jul. 15, 2010

Related U.S. Application Data

(60) Provisional application No. 60/924,998, filed on Jun. 7, 2007.

(51) Int. Cl.
*C12Q 1/02* (2006.01)
(52) U.S. Cl.
USPC .................. 435/29; 435/283.1; 435/288.7
(58) Field of Classification Search
None
See application file for complete search history.

(56) References Cited

U.S. PATENT DOCUMENTS

2004/0070757 A1   4/2004   Moore

OTHER PUBLICATIONS

Chirila T.V. et al., The Use of Hydrophilic Polymers as Artific Ial Vitreous, Prog. Polym. Sci., 1998, vol. 23, pp. 475-508.*
Clasen C. et al., Determination of viscoelastic and rheo-optical material functions of water-soluble cellulose derivatives, Prog. Polym. Sci., 2001, vol. 26, pp. 1839-1919.*
Heidemann S. R. et al., Towards a regional approach to cell mechanics, TRENDS in Cell Biology, 2004, vol. 14, No. 4, pp. 60-166.*
Josheph D.D. et al., Motion of Particles Settling in a Viscoelastic Fluid, Proceedings of the Second International Conference on Multiphase Flow, Kyoto, Japan, Apr. 3-7, 1995, pp. 1-9.*
Bransky, Avishay et al., "An automated cell analysis sensing system based on a microfabricated rheoscope for the study of red blood cells physiology," Biosensors and Bioelectronics 22(2):165-169 (2006).
Bransky, Avishay et al., "Correlation between erythrocytes deformability and size: A study using a microchannel based cell analyzer," Microvascular Research 73(1):7-13 (2007).
Bransky, Avishay et al., "The rheologic properties of erythrocytes: a study using an automated rheoscope," Rhelogica Acta 46(5):621-627 (2007).
Faivre, Magalie et al., "Geometrical focusing of cells in a microfluidic device: an approach to separate blood plasma," Biorheology 43(2):147-159 (2006).
Ho, B. P. et al., "Migration of rigid spheres in a two-dimensional unidirectional shear flow of a second-order fluid," Journal of Fluid Mechanics 76(4):783-799 (1976).
Wu, Zhigang et al., "Rapid mixing using two-phase hydraulic focusing in microchannels," Biomedical Microdevices 7 (1):13-20 (2005).
International Search Report of PCT/IL2008/000772 mailed Jan. 21, 2009.

* cited by examiner

*Primary Examiner* — Jon P Weber
*Assistant Examiner* — Satyendra Singh
(74) *Attorney, Agent, or Firm* — Finnegan, Henderson, Farabow, Garrett & Dunner, LLP

(57) ABSTRACT

Provided is a method of focusing particles. The method includes: providing a suspension of the particles in a suspending medium; and flowing the suspension along a channel, such that the flowing suspension occupies a certain volume that has at least one cross-sectional dimension smaller than 100 μm. The suspending medium has such viscoelastic properties, that flowing the suspension in the channel directs at least some of the particles towards a focus region, enclosed in said certain volume.

22 Claims, 9 Drawing Sheets

METHODS FOR VISCOELASTIC FOCUSING OF PARTICLES

RELATED APPLICATIONS

This application is the U.S. national stage of PCT/IL2008/000772, filed Jun. 5, 2008, which claims the benefit of U.S. provisional patent application No. 60/924,998, filed Jun. 7, 2007, the contents of each of which are herein incorporated by reference for all purposes.

FIELD AND BACKGROUND OF THE INVENTION

The present invention, in some embodiments thereof, relates to flow cytometry, and more particularly, but not exclusively, to fluorescene-activated cell sorting (FACS).

Flow cytometry is a technique for simultaneous multiparametric analysis of physical and/or chemical characteristics of single cells. Flow cytometry allows for counting, examining, and sorting cells (or other microscopic particles) and provide multiparametric analysis of the physical and/or chemical characteristics of single particles. The cells to be analyzed flow towards an inspection point, and this flowing is designed such that the particles arrive at the inspection point single file, so each particle is analyzed individually.

One particular flow cytometry technique is termed Fluorescence-Activated Cell Sorting (FACS). FACS provides sorting a heterogeneous mixture of biological cells or other particles into two or more containers, one cell at a time, based upon the specific light scattering and fluorescent characteristics of each cell. It is a useful scientific instrument as it provides fast, objective and quantitative recording of fluorescent signals from individual cells as well as physical separation of cells of particular interest.

The technology has applications in a number of fields, including molecular biology, pathology, immunology, plant biology and marine biology.

For instance, in the field of cell biology and immunology it is used with fluorescence tagged antibodies, which bind to specific target cells and allow quantitative analysis of the antigens in the cytometer. This method is widely used to study protein expression and localization, cell surface antigens quantification (CD markers on blood cells in different clinical pathologies, for instance, leukemia), intracelluar and nuclear antigens (activation of transcription factors such as FoxP3 in T-regulatory cells), cell viability (quantification of apoptotic cells by Annexin/PI staining), and others.

Flow cytometry and FACS also have broad application in medicine, especially in transplantation, hematology, tumor immunology and chemotherapy, genetics and sperm sorting in IVF.

Generally, in a flow cytometer a beam of light is directed onto a stream of fluid, where the particles are aligned in the fluid one by one. A number of detectors are aimed at the point where the stream passes through the light beam. Each suspended particle passing through the beam interacts with the light in some way (for instance, scatters the light), and the light from the particle is picked up by the detectors. The detected light is analyzed to provide various types of information about the physical and chemical structure of each individual particle.

A flow cytometer typically has 5 main components:
a flow cell, where liquid stream carries and aligns the cells so that they pass single file through the light beam for sensing;
a light source;
a detector
an amplification system; and
a computer for analysis of the amplified detected signals.

Aligning the particles in the flow cell is achieved by applying to the particles an external force. One method of applying external force that is used in commercially available flow cytometers is termed in the art "sheath flow". Other methods include applying to the particles light and ultrasound.

SUMMARY OF THE INVENTION

The present invention, in some embodiments thereof, relates to flow cytometry, and more particularly, but not exclusively, to fluorescene-activated cell sorting (FACS).

An aspect of some embodiments of the invention relates to aligning particles so they pass single file, for instance, through a light beam of a flow cytometer.

Thus, an aspect of some embodiments of the invention concerns a method of focusing particles, the method comprising:
providing a suspension of the particles in a first suspending medium; and
flowing the suspension along a channel having at least one cross-sectional dimension smaller than 100 µm;
wherein the first suspending medium has such viscoelastic properties that flowing the suspension in the channel increases the concentration of the particles in a focus region inside said channel.

In exemplary embodiments, the focus region is at half the height of the channel.

In some embodiments, said focus region has a cross-section perpendicular to the length of the channel that has the same shape as the channel's cross-section at the same place, but smaller.

Optionally, the focus region is coaxial with the channel.

In some exemplary embodiments of the invention
said suspension comprises particles of various sizes; and
said viscoelastic properties are such that flowing the suspension in the channel preferentially directs larger particles towards the focus region.

Optionally, providing a suspension comprises:
obtaining a suspension of the particles in a second suspending medium; and
exchanging said second suspending medium with said first suspending medium.

Optionally, providing a suspension comprises:
providing a plurality of suspending media having various viscoelastic properties
selecting said first suspending medium from said plurality of suspending mediums responsive to the viscoelastic properties of the media; and
suspending the particles in the selected suspending medium.

In some embodiments, selecting comprises selecting responsive to the size of the particles.

In exemplary embodiments, providing a suspension comprises:
suspending the particles in a trial suspending medium;
flowing the suspension along a microchannel, such that the flowing suspension has at least one dimension smaller than 100 µm;
estimating focusing quality; and
changing the viscoelastic properties of said trial suspending medium so as to improve focusing quality.

Optionally, the method comprises
flowing the suspension at a certain flow-rate;
estimating focusing quality; and
enlarging said flow rate so as to improve focusing quality.

Optionally, enlarging the viscoelastic properties of said trial suspending medium comprises adding to the suspension a high molecular weight polymer.

Optionally, the channel's depth is less than 100 μm.

Optionally, the channel's width is less than 100 μm.

Optionally, the channel has depth, and width, each smaller than 100 μm.

In some exemplary embodiments, the particles are cells.

In some exemplary embodiments, the second suspending medium comprises blood serum.

There is also provided, in accordance with another aspect of some embodiments of the present invention, a system for focusing flowing particles, the system comprising:

a channel having walls and a bottom between the walls;

a fluid source comprising sample fluid; and a fluid direction system configured to direct the sample fluid from the fluid source into the channel through an inlet, wherein said sample fluid comprises the particles suspended in a liquid, said liquid having viscoelastic properties alleviating the need to apply an external force field for focusing the particles in a focus region.

In exemplary embodiments, the focus region is at half the height of the channel.

In accordance with some exemplary embodiments, the system comprising:

a light source providing an interrogating light beam in sensory communication with said focus region at an inspection zone downstream from said inlet; and a detector which is configured to detect the particles in the inspection zone using the interrogating light beam.

Optionally, the particles comprise cells.

In some embodiments the channel has at least one cross-sectional dimension of between 5 and 100 μm.

Optionally, said at least one cross-sectional dimension comprises a dimension of a cross-section perpendicular to a bottom of said channel.

Optionally, the channel has a bottom and walls, and the distance between the walls is larger than 100 μm.

Optionally, the system comprises a plurality of fluids, each with different viscoelastic properties, and instructions to use each fluid for focusing particles of different size.

In accordance with some embodiments of the invention there is provided a comprising:

a plurality of fluids, each packed separately in a package carrying an indication of a size range; and instructions to use each of said plurality of fluids for focusing particles of the indicated size range.

An aspect of some embodiments of the invention concerns a method of evaluating elasticity of a liquid, the method comprising:

adding to the medium particles of monodispersed size distribution to obtain a suspension;

flowing the suspension in a channel having at least one cross-sectional dimension of 100 μm or less;

obtaining a spatial distribution of the particles after the particles flow in the channel along a given distance; and analyzing the spatial distribution to obtain the elasticity of the medium.

Optionally, analyzing comprises analyzing responsive to the medium's viscosity, and the method comprises obtaining the medium's viscosity.

Optionally, obtaining the medium's viscosity comprises measuring the medium's viscosity.

In some embodiments, the volume fraction of the particles in the obtained suspension is between 0.001% and 1%.

Optionally, volume fraction of the obtained suspension is 0.1%.

There is also provided, in accordance with an aspect of some embodiments of the invention a method of evaluating interactions between particles and binders comprising:

focusing the particles at a layer above a bottom of a channel; and flowing the focused particles above binders immobilized to said bottom.

Optionally, the particles are focused such that centers of at least 90% of the particles are in a layer having a thickness of less than half the height of the channel.

In some embodiments, focusing the particles comprises focusing in a method according to embodiments of the present invention.

In some embodiments, evaluating interactions between particles and binders performing the above method a plurality of times, each time with a channel of different depth.

An aspect of some embodiments of the present invention concerns a device for evaluating interactions between particles and binders, the device comprising:

a plurality of systems, each according to an embodiment of the invention, and at least one of said systems has a channel with the binders immobilized to at least a portion of the bottom of said channel.

Optionally, said plurality of systems have a common fluid source.

Optionally, said plurality of systems have a common fluid directing system.

Optionally, the device has a controller for controlling the flow rate of fluid into the channel in each of the systems independently of the others.

Optionally, not all the channels are of the same depth.

Optionally, each of the channels is of a different depth than all the others.

In some embodiments, the device is configured to focus the particles with the same focusing quality in all the channels.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only; with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 8A shows results for 8 μm-diameter particles; and FIG. 8B shows results for 5 μm-diameter particles. The solid lines serve to guide the eyes.

DESCRIPTION OF SPECIFIC EMBODIMENTS OF THE INVENTION

Overview

Figure 1:
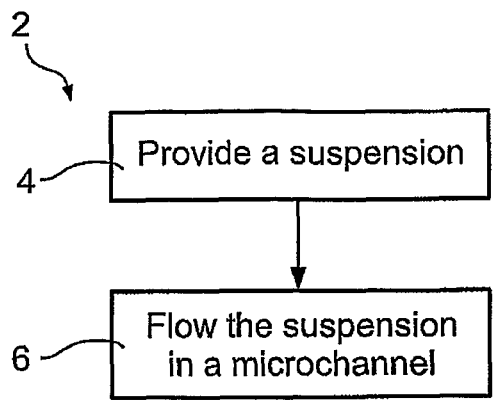
FIG. 1 is a flow chart of actions taken in a method of focusing particles according an exemplary embodiment of the invention.

The present invention, in some embodiments thereof, relates to flow cytometry, and more particularly, but not exclusively, to fluorescene-activated cell sorting (FACS).

Some embodiments provide methods or devices for particle focusing microfluidic flow.

Some embodiments of the invention may be practiced with channels that are generally not considered to be microfluidic. The same focusing quality can be obtained at distance x/d from the inlet with channels of any given dimension, as long as the following expression maintains its value:

$$\left(\frac{a}{d}\right)^2 \left(\frac{\overline{U}}{d}\right)^{\beta-n}$$

Wherein a is the particle's radius, d is half the smallest dimension of the channel, $\overline{U}$ is the flow rate, and β and n characterize the viscoelastic properties of the suspending medium. Given the above, further details on the scaling-up possibilities are apparent from the theoretical analysis provided below under the heading "theoretical guiding".

In exemplary embodiments, focusing comprises flowing the particles in a suspending medium having such viscoelastic properties that alleviate the need to apply external fields on the particles in order to focus them.

In some exemplary embodiments, the particles comprise cells, for example, blood cells, bacteria, and/or cancerous cells. Optionally, the particles comprise macromolecules, vesicles, microbeads covered with antibodies specific to soluble factors such as ligands, shaded receptors, antigens and antibodies. Nevertheless, the term 'particles' is not necessarily limited to these examples.

In some exemplary embodiments, the particles flow inside a channel in a suspending medium, and concentrate in a certain portion of the channel, termed herein "the focus region". Optionally, the focus region is at the center of the channel, for example, in a volume extending perpendicularly from the channel's bottom at the center of the bottom.

It should be noted that the term "channel" is used herein to denote any structure having at least one dimension smaller than 100 μm and a length that is much larger than 100 μm, for example 1 mm, 10 mm, 50 mm, 100 mm, 1000 mm, or any intermediate or longer length. In some embodiments, a channel is a groove on an upper surface of a solid body. In some embodiments, a channel is a tube. A cross-section of a channel, perpendicular to the channel's length is optionally rectangular, square, rounded, or spherical.

Channels of rectangular or square cross-sections are optionally obtained using lithography, for example, soft lithography or photolithography. This kind of manufacture method allows easy and accurate mass manufacture of bodies carrying microchannels, for instance, lab-on-chips.

The focusing quality is optionally obtained with channels of larger smallest dimension, if the channel is similarly longer and the particles are similarly larger. If the channel has a smallest dimension that is larger than 100 μm and the particles are about 1-10 μm, the focusing quality deteriorates.

Focusing at the center of the channel, may be advantageous over focusing in other areas of the channel in several aspects. For instance, at the center of the channel the flow velocity is higher than off-center. Therefore, particles focused at the center of the channel flow faster, and may be handled in higher throughputs. In another instance, when the treated particles are small Brownian particles, for example, smaller than 1 μm, they tend to diffuse perpendicularly to the flow direction and the transverse diffusivity is enhanced by the shear (an effect known in the art as Taylor dispersion). This tendency is minimal at the center of the channel where the shear-rate is minimal, and therefore, faster movement of the particles along the flow direction can be achieved with minimal sample width broadening due the transverse shear-augmented diffusion. In another example, if the particles have a tendency of adsorbing to the channel's walls, focusing the particles in the center minimizes their interactions with the wall and decreases adsorption/adhesion phenomena.

In some embodiments of the invention, the focusing is horizontal, that is, the particles are focused at a horizontal region of limited depth near half the depth of the channel. Horizontal focusing may be advantageous, for instance, when the particles are to be analyzed optically, with an optical device positioned above the channel. In such cases, the horizontal focusing may bring all the particles to be within the focus of the optical analyzer, allowing for faster analysis of the particles than would be allowed if the particles are focused vertically. Some embodiments of the invention are practically independent of gravitation. Nevertheless, because in some embodiments particles are analyzed using a light beam, it may be convenient to interpret the terms "horizontal" and "vertical" to denote alignment with the light beam, for instance, defining that the light beam arrives along the vertical direction.

Horizontal focusing is optionally obtained when the vertical dimension of the channel (that is, the channel's height), is 100 μm or less.

In some embodiments, the focusing is in a vertical direction, that is, the particles concentrate in a focusing region that is perpendicular to the channel's bottom, at about half the width of the channel. Vertical focusing is optionally obtained when the horizontal dimension of the channel (that is, the channel's width), is about 100 μm or less.

In some embodiments, a three-dimensional (3-D) focusing takes place, in the sense that the particles flow away of the bottom and top wall of the channel and also away of the walls of the channel, and concentrate in a volume that does not extend to touch any of the channel's walls. Two-dimensional focusing is optionally obtained with channels that have both height and width of about 100 μm or less.

Optionally, three dimensional focusing is obtained with a channel that is 100 μm or less in one of its dimensions, and in the other dimension focusing is obtained by other methods, which as such are not necessarily in accordance with embodiments of the present invention, for instance, sheath-flow focusing, also known as hydrodynamic focusing.

Optionally, sheath flow focusing or other known focusing method is used in combination with viscoelastic focusing.

In some embodiments, the focused particles are lined up, optionally one by one, such that the centers of a substantial portion of the particles are within a cylinder having a radius that is about the same as a typical radius of the particles. In some embodiments such focusing considerably reduces the longitudinal dispersion of particles and yields higher throughputs. The improved throughput is possibly because the particles focus at the center, where the velocity of the pressure-driven flow is expected to be maximal, Optionally, the substantial portion is 90% or more of the particles, optionally more than 95%, optionally more than 99%.

Optionally, the radius of the cylinder is less than 120% of the particles' typical radius.

In case of non-spherical particles, the particles typical size corresponds to the smallest dimension of the particle. For instance, cylindrical particles with a base having a diameter of 1 μm and a height of 10 μm focus similarly to spherical particles of 1 μm diameter.

In exemplary embodiments of the invention, a method of focusing the particles includes flowing a suspension of the particles in a long channel, having at least one dimension smaller than 100 μm.

Optionally, substantial focusing occurs after flowing the particles along a relatively short distance. For instance, focusing of 90% of the particles to within a cylinder having a radius larger in 20% than the particles radius can occur after flowing the particles along 10 cm or less, for example, after 5 cm, 2 cm, or 1 cm.

In an exemplary embodiment, the suspension comprises the particles and a suspending medium, and the suspending medium is selected and/or manipulated to have viscoelastic properties that result in a desired focusing and alleviates the need to apply external fields on the flowing suspension to obtain the focusing.

In some exemplary embodiments of the invention, the suspending medium has the same density everywhere inside the channel. Optionally, no density gradient is required for focusing.

Manipulating the viscoelastic properties of the suspending medium optionally comprises adding to the suspending medium a modifier, which modifies the viscoelastic properties of the suspension. Optionally, the modifier is a high molecular weight polymer, for example, a polymer having molecular weight of between about 50 and about 1000 kiloDaltons. Preferably, the modifier is added in amounts that are soluble in the dispersing medium. Optionally, the modifier is bio-compatible. This option may be advantageous when the particles comprise biological material, such as living cells or microbeads.

Examples of some modifiers useful in various embodiments include, but are not limited to polyacrylamide (PAA) polyethyleneglycol (PEG), polysucrose (Ficoll™), polyglucose (Dextran), methylcellulose, and xanthan gum.

Some viscoelastic properties that might affect the focusing include: viscosity, elasticity, and, in case the suspending medium is not Newtonian, the shear thinning of the medium.

Viscosity is optionally measured, in Pascal-sec or Poise. Generally, higher viscosity results in less efficient focusing.

Elasticity is optionally defined by the $1^{st}$ normal stress difference, usually designated as $N_1$. $N_1$ is related to the storage or elasticity modulus, G' that can be measured experimentally using commercially available rheometers. Generally, higher elasticity results in more efficient focusing.

Sheer thinning is the change in viscosity in response to change in shear rate. Generally, higher sheer thinning results in more efficient focusing.

Particle focusing with a suspending medium having such viscoelastic properties that alleviate the need to use external force fields to obtain the focusing is referred herein as "viscoelastic focusing".

In some embodiments, the focusing is affected by the flow rate of the suspension inside the tube. Generally, higher flow rate results in more efficient focusing. In some other embodiments, however, the focusing is nearly independent of the flow rate. In the latter, the need to precisely control the flow rate is alleviated, and systems utilizing flow-rate independent focusing may be made simpler and more robust than embodiments that use flow-rate dependent focusing. For instance, flow rate can be much less accurate in flow-rate independent embodiments. The conditions for obtaining flow-rate independent focusing are discussed in the context of FIG. 9A and under the heading "theoretical guiding" below.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 is a flow chart of actions taken in a method (2) of focusing particles, according an exemplary embodiment of the invention.

Action 4 comprises providing a suspension of the particles in a suspending medium. The suspending medium has such viscoelastic properties, that when the suspension flows in a channel of suitable dimensions at least some of the particles are directed towards a focus region within the channel.

In some embodiments, the focus region cross-section perpendicular to the channel's length has width that is substantially equal to the width of the channel, and length that is much smaller than the depth of the channel. In these cases the focusing is referred herein as "horizontal".

In some embodiments, the focus region cross-section perpendicular to the channel's length has depth that is substantially equal to the depth of the channel, and width that is much smaller than the width of the channel. In these cases the focusing is referred herein as "vertical".

In some embodiments, the focus region cross-section perpendicular to the channel's length has height that is substantially smaller than the depth of the channel, and width that is much smaller than the width of the channel. In these cases the focusing is referred herein as 3-D.

In an exemplary embodiment of the invention, the channel's depth is smaller than 100 μm, with more shallow channels allowing for earlier focusing (under otherwise similar conditions). Two factors that limit the depth of the channel are the tendency of too small channels to clog, and the higher inlet pressure required in order to flow fluids in small channels.

Optionally, the channel also has width smaller than 100 μm, in which case, a 2-D focusing is obtained, and the particles focus away of the channel's bottom and top wall and also away of the channel's vertical walls. In 3-D focusing, the focusing region optionally has a cross-section similar to that of the channel, but smaller. Optionally, a 3-D focusing region is coaxial with the channel.

Action 6 comprises flowing the suspension along the channel.

In some exemplary embodiments, method 2 results in arranging the particles one by one, allowing their inspection in a flow cytometer.

In some embodiments, the suspension comprises particles of various sizes, and the viscoelastic properties of the suspending liquid are such that flowing the suspension in the channel selectively directs particles of a given size towards the focus region. For instance, in some embodiments, discussed in relation with FIGS. 5A and 5B below, 95-99% of particles of 8 μm diameter are directed to the focusing region, while only 35-40% of particles of 5 μm diameter are directed to the same focusing region.

Exemplary Ways of Providing the Suspending Medium

In some embodiments, the particles are dry, and are suspended in a suspending medium selected in accordance with the medium viscoelastic properties.

In some embodiments, the particles are provided when suspended in a non-suitable medium.

Optionally, a suitable suspending medium is added in excess, so as to control or eliminate the effect of the non-suitable viscoelastic properties of the provided suspending medium.

Alternatively or additionally, the suspending medium is exchanged with another suspending medium, which has suitable viscoelastic properties.

For instance, in many embodiments blood is treated, and the particles to be sorted are blood cells, provided suspended in blood serum.

In some embodiments, saline is added to the blood. Optionally, the amount of added serum is about 15, 20, or 25 times the amount of blood.

In some embodiments, the blood serum is exchanged with saline. Optionally, such exchange comprises centrifuging the blood sample, extracting the plasma, and suspending the extracted plasma with saline.

In some embodiments, the saline used to replace the serum and/or the saline added to the serum comprises a modifier, as described above.

In some embodiments, a plurality of optional suspending mediums are provided, and one of them is selected in accordance with the suspending medium viscoelastic properties and the properties of the particles that should be focused or sorted, for instance, the size of the particles.

Optionally, the suspending medium is selected responsive to particles' size and deformability. Optionally, deformability is used to define an effective radius, and the suspending medium is selected responsive to the defined effective radius.

Optionally, different suspending media are provided for particles of different sizes and deformability.

In some embodiments, a trial suspending medium is first used, and the particles are flown in a microchannel in the trial suspending medium along some path, and focusing quality is estimated. Focusing quality is optionally defined as the percentage of the particles that focus at a focusing region of given dimensions after flowing in a channel a given distance at a given flow-rate.

If the focusing is insufficient, the suspending medium is optionally amended. Optionally, the suspending medium is amended by adding to it a modifier, which modifies the viscoelastic properties of the suspending medium. Optionally, the modifier comprises a high molecular weight polymer such as polyacrylamide (PAA), which is known to enhance elasticity of liquids in which it is dissolved. Optionally or additionally, the modifier comprises a high molecular weight polymer, for instance, glycerol, which is known to change the viscosity of liquids in which it is dissolved. Optionally, one polymer modifies both viscosity and elasticity. Optionally, one or more polymer is used to modify elasticity and one or more polymer is used to modify viscosity.

In an exemplary embodiment of the invention focusing quality is estimated based on the width of the thinnest layer at which the centers of 95% of the focused particles are located. Optionally, the thinner is the layer, the better is the focus. Optionally, the focusing quality is estimated based on the fraction of the focused particles, the centers thereof lies within a layer of a given thickness.

Additionally or alternatively, focusing quality is estimated based on the length of a path that particles travel in the channel to focus to a certain degree. For example, in an embodiment, focusing is considered better if 95% of the particles concentrate at a 2 μm thick layer at 20 mm from the inlet than if 95% of the particles concentrate at a 2 μm thick layer at 50 mm from the inlet.

Exemplary System

Figure 2A:
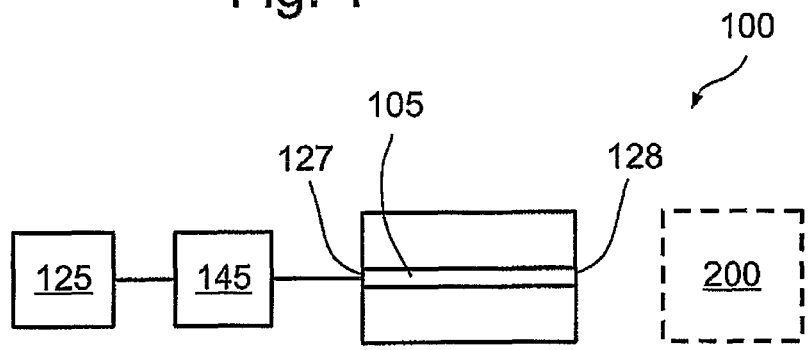
FIG. 2A is a schematic illustration of a system for focusing flowing particles, in accordance with an exemplary embodiment of the invention.

FIG. 2A is a schematic illustration of a system 100 for focusing flowing particles, in accordance with an exemplary embodiment of the invention. The figure shows a channel (105) in fluid communication with a fluid source 125 through a fluid direction system 145. Fluid direction system 145 is provided for directing sample fluid from fluid source 125 into channel 105 through input 127 towards inspection zone 128. Optionally, fluid direction system 145 comprises a syringe pump, the piston of which is pushed at a constant and controlled rate. An example of a commercially available suitable fluid direction system is KDS 210 Scientific of KD Scientific Inc. (USA).

Figure 2B:
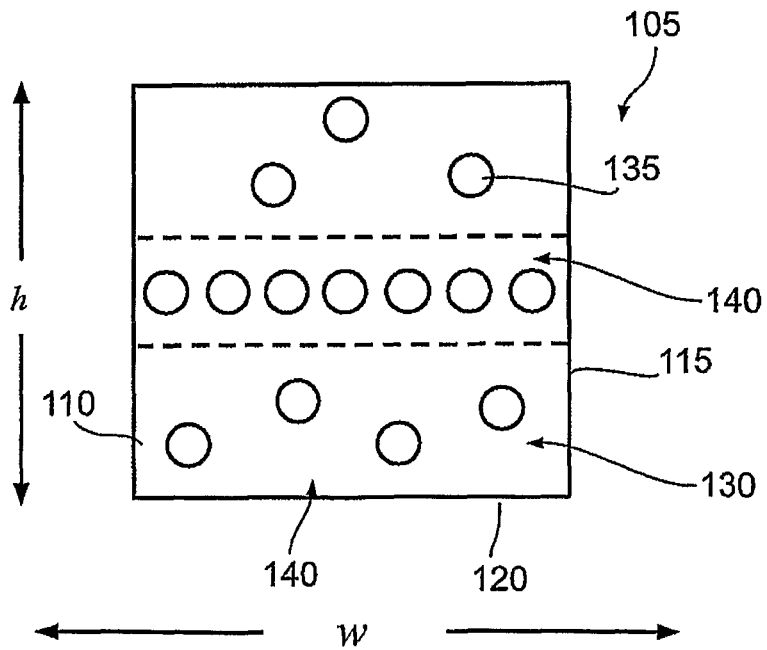
FIG. 2B is a schematic illustration of a channel according to the embodiment of the invention.

FIG. 2B is a schematic illustration of channel 105. The figure shows channel 105 to have walls 110 and 115, bottom 120 and top wall 122.

Sample fluid 130 comprises particles 135, suspended in a suspending medium. The suspending medium has viscoelastic properties that facilitate focusing of particles 130 in a portion 140 of channel 105, and alleviates the need to apply an external field for obtaining the focusing. Nevertheless, in some embodiments, an external field is applied as known in the art, optionally in order to strengthen the focusing, alternatively or additionally, to focus the particles along an additional direction.

In operation, fluid 130 is directed into channel 105 by fluid directing system 145 and particles 135 are directed to a focus region 140, enclosed in channel 105.

Channel 105 is a microchannel, having a height h, perpendicular to bottom 120, and width w, between walls 110 and 115. At least one of height h and width w is smaller than 100 μm, optionally between about 5 μm and about 100 μm, for example 10, 20, 50, 80, or 100 μm. Optionally, the distance w between walls 110 and 115 is also smaller than 100 μm. Optionally, one of h or w is larger than 100 μm. In one exemplary embodiment w is 1 mm and h is 50 μm.

Figure 3:
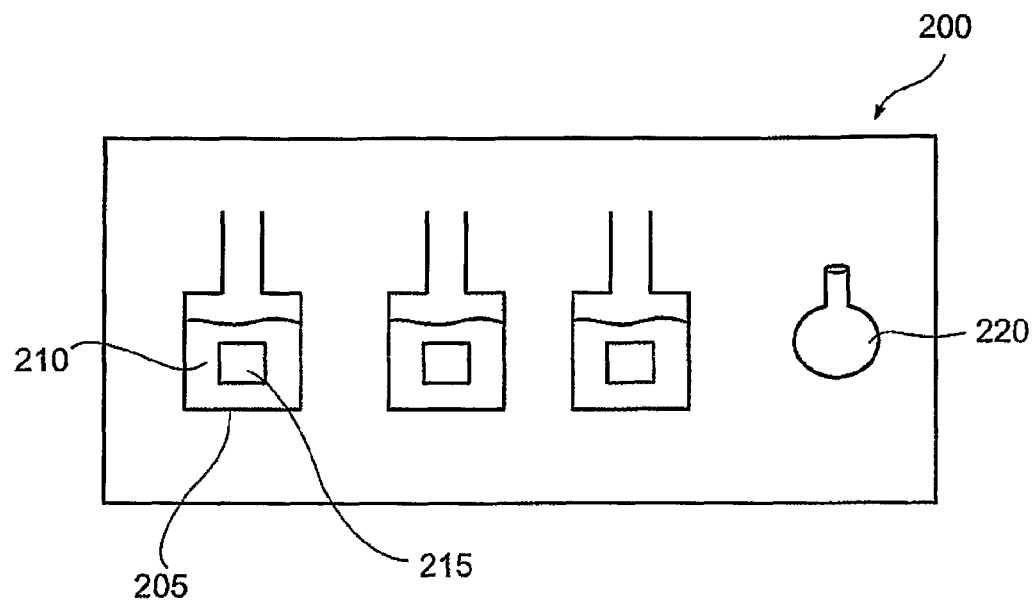
FIG. 3 is a pictorial depiction of a kit according to an embodiment of the invention.

Optionally, system 100 also comprises a kit 200, pictorially depicted in FIG. 3. Kit 200 comprises a plurality of packages 205, which in the depicted embodiment are bottles, and each package contains a suspending medium 210, which has viscoelastic properties suitable for focusing particles of a give size. Each of bottles 205 carries a label 215, indicating the size of particles to be suspended therein for focusing with system 100. Optionally, the label indicates different particle sizes for different flow rates. Optionally, the label indicates different particles sizes to systems of different dimensions.

Optionally, kit 200 (and/or system 100) also comprises instructions, with what suspending medium should which particles be focused. Optionally, the indication mentions a particle size. Additionally or alternatively, the indication mentions a certain type of cells, for instance: red blood cells, leukocytes, cancerous cells, and/or bacteria.

Exemplary Suspending Mediums

In some embodiments of the invention, the suspending medium is selected or chosen in a trial-and-error method.

For example, the viscoelastic properties of phosphate buffered saline (PBS) may be modified by adding thereto PVP of 360 kilo-Dalton. Optionally, the PVP is added to form about 2%, 5%, 8% of the dispersing medium, or any intermediate concentration. In another example, the viscoelastic properties of PBS are modified by adding similar amounts of Dextran having molecular weight greater than 70 kilo-Dalton. Additionally or alternatively 5-100 ppm of PAA, and/or methylcellulose are added to the saline.

In some embodiments, theoretic analysis is used to guide the trial and error method. For instance, the viscoelastic properties required for focusing particles of a certain size in a given channel is calculated, and medium with similar viscoelastic properties is used as a trial suspending medium, and if necessary, modified as explained above.

Exemplary Applications

Exemplary FACS Machine

Figure 4A:
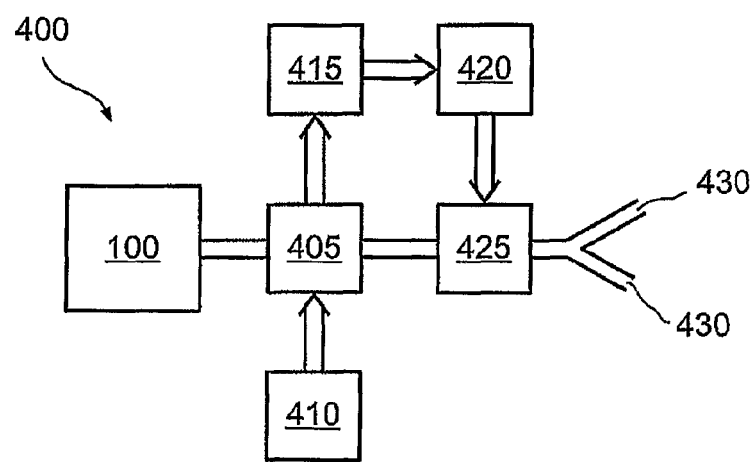
FIG. 4A is a schematic illustration of a FACS machine according to an embodiment of the invention.

FIG. 4A is a schematic illustration of a FACS machine 400, utilizing a system according to an embodiment of the invention. Machine 400 comprises particles focusing system 100, optionally of the kind described above and shown in FIGS. 2A and 2B. The fluid in the fluid source comprises particles suspended in a suspending medium of suitable viscoelastic properties. System 100 outputs particles from the fluid source, after the particles flow through channel 105 to an inspection zone 405 (128 in FIG. 1A).

Machine 400 also comprises a light source 410, pointing a light beam on inspection zone 405, so as to illuminate particles that arrive from system 100 to the inspection zone. Optionally, the focusing provided by system 100 is such that the particles arrive to the inspection zone one by one. Each particle interacts with light arriving from light source 410, optionally by scattering the light. Additionally or alternatively, some of the particles also emit fluorescence.

Optionally, light source 410 illuminates the particles from above channel 105. In embodiments where the focus zone is horizontal (i.e. parallel to bottom 120) to and at the middle of the channel's height, the light source is tuned to focus on the layer where the particles focus, attending to receive scattered light and/or fluorescence from particles distributed all over the width of channel 105 and concentrated at the mid-height of the channel. upper side of channel 105. The scattered and/or emitted light is detected by a detector (415); and analyzed with a computer 420.

Optionally, computer 420 controls a switch 425, that directs each particle to one of a plurality of destinations 430, responsive to the analysis results. For instance, particles of stronger fluorescent are directed to one destination, and particles of weaker fluorescence—to another.

Exemplary Rheological Measurements

An aspect of some embodiments of the invention concerns measuring the rheological properties of a medium, optionally, to unprecedented accuracy. The method is based on the relation between the elasticity of a medium and the degree of focusing achievable with the medium.

Figure 4B:
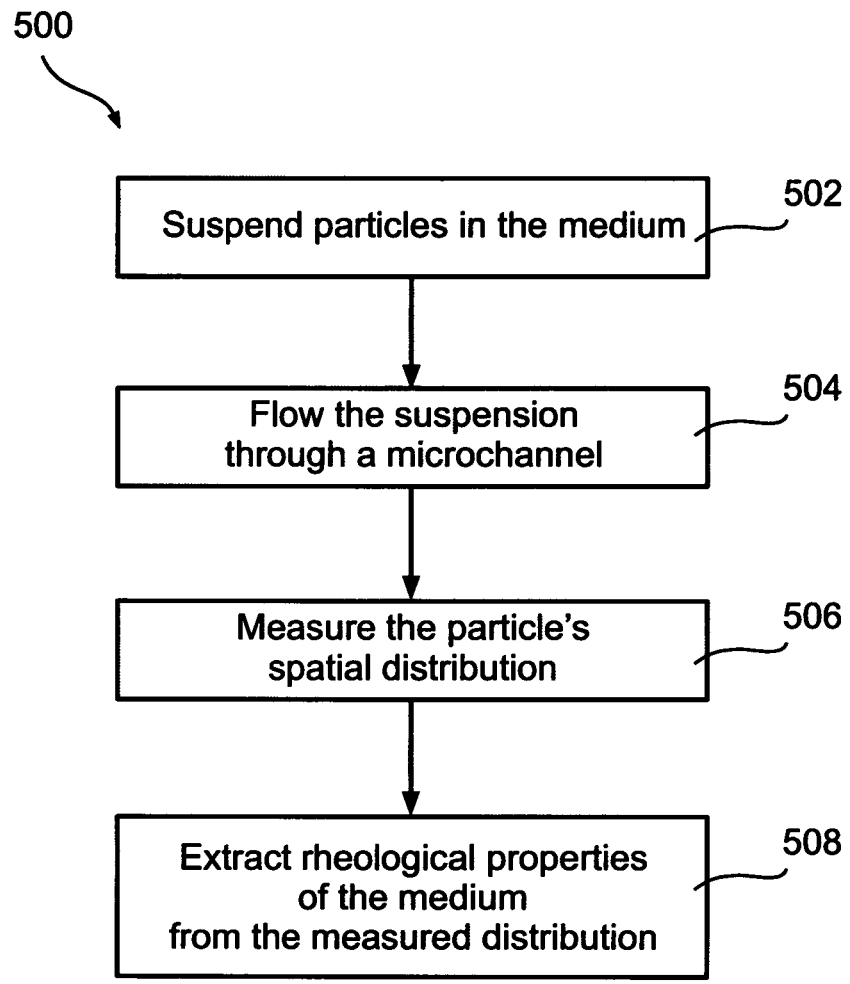
FIG. 4B is a flowchart of actions taken in a method of measuring rheological properties of a medium according to an exemplary embodiment of the invention.

FIG. 4B is a flowchart of actions taken in a method 500 of measuring rheological properties of a medium according to an exemplary embodiment of the invention.

At 502, particles of known size and sharp size distribution are suspended in the medium. Optionally, the amount of particles is such that the volume concentration of the obtained suspension (that is the fraction of the volume of the suspension which is occupied with particles) is between about 0.01% and 1%, for example, 0.1%.

At 504, the suspension obtained in 502 is flown through a microchannel.

At 506, the spatial distribution of the particles at some distance from the inlet is measured, for instance, as described below under the section headed "theoretical guiding".

At 508, the rheological properties of the suspending medium are extracted from the measured spatial distribution using the equations provided below under the section headed "theoretical guiding".

Optionally, the analysis uses data on the viscosity of the medium. Optionally, the method comprises measuring such data.

Optionally, method 500 allows measurement of the elasticity of the medium in accuracies in the order of ±0.01 to ±0.001 Pascal, compared to commercially available rheometers that provide accuracy of ±10 Pascal.

Exemplary Binding Assay

Many types of particles, for examples, cells and macromolecules, exhibit tendency to adhere to surfaces. This tendency may sometimes be used for analyzing an assay of particles. For instance, in an exemplary embodiment, the tendency of monoclonal antibodies to bind to immobilized antigens or the tendency of receptors to bind to ligands immobilized at the interior surface of channels are studied. In another exemplary embodiment, the tendency of leukocytes to bind to immobilized ligands (known in the art as in-vitro rolling assays) is studied.

In an exemplary embodiment, particles are focused in a suspending medium in a thin layer at a given height above the bottom of the channel, and the capability of the focused particles to attach to binders immobilized to the bottom is studied.

In the latter case, focusing may serve as a particularly helpful tool for fine-tuning of the effective interaction range between the freely suspended particles and the binders immobilized at the channel bottom. Such fine-tuning may be useful in improving the spatial resolution of the assay.

Optionally, the channel has a first portion, near the inlet, with no binder immobilized on the bottom, and a second portion, downstream of the first portion, with immobilized binders.

Optionally, the first portion is long enough to allow a majority, for example, 95% of the particles to have their centers lie in a layer that is much thinner than the channel's height, for instance, 5% of the height.

Optionally, the second portion is of the same height as the first portion and particles that are not attracted to the immobilized binder moves in the second portion substantially the same as it moved in the first portion. Optionally, the second portion is long enough to bind a majority, for instance 95% of all the particles that may bound to the binder, and only particles that do not bind exit from the second portion.

Optionally, a plurality of channels is used, each channel with a different height, such that the interaction-distance between the binders immobilized to the bottom and the particles, focused at the a thin layer at half the height, based on the smallest channel height where particles adherence to the binders is below a first threshold and the largest channel height where particles adherence to the binders is above a second threshold. For instance, the interaction distance may be defined as the midpoint between the smallest height at which less than 5% of the particles adsorb and the largest height at which at least 95% of the particles adsorb.

Optionally, the interaction distance between the binder and the particles is evaluated based on binding at a certain distance from the beginning of the second portion.

Optionally, all the channels have first portions of the same length. Optionally, the different channels have first portions designed to focus particles to the same extent in all the channels. Optionally, this is achieved with first portions of different lengths, with longer first portions associated with deeper channels. Optionally or additionally, having all the first portions with the same focusing power is achieved with tuning the flow directing systems directing fluid to the different channels to direct fluid at higher flow to deeper channels.

Figure 4C:
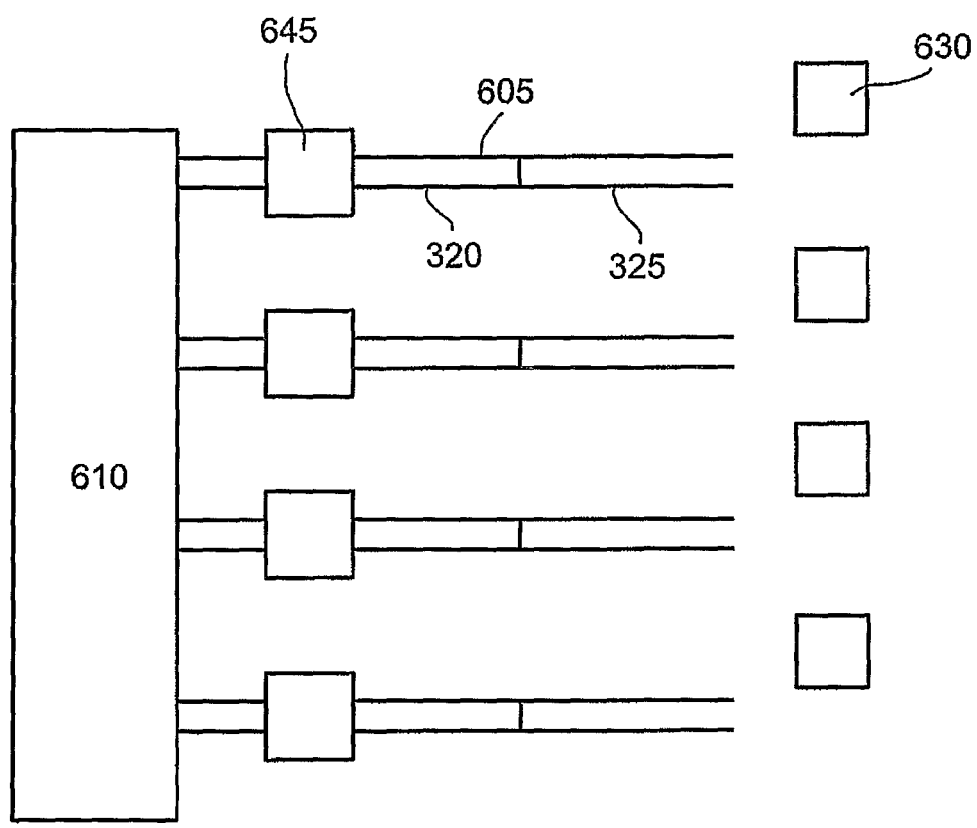
FIG. 4C is a schematic illustration of a device for studying particle-binder interaction in accordance with an exemplary embodiment of the invention.

FIG. 4C is a schematic illustration of a device for studying particle-binder interaction in accordance with an exemplary embodiment of the invention.

The device 600 comprises a plurality of channels 605, each receiving sample fluid from a reservoir 610. Optionally, each channel 105 has its own, flow directing system 645, which is optionally controllable to direct sample fluid into the channel associated therewith in a flow rate independent from the flow rates at which fluid is directed to any of the other channels.

In the depicted embodiment, each channel 605 has a first portion 620. Optionally, each flow directing system is operated such that at the end of the first portion, the centers of about 90% of the particles occupy a thin layer at the middle of the channel's height.

Also shown in the depicted embodiment are second portions 625, where binders are immobilized to the bottom of the channel. Above each channel, at some distance after the beginning of the second portion, there is shown a camera, 630 that images the particles in the channel below the camera, to evaluate the number of particles that arrive at this point.

Optionally, the amount of binding is evaluated based on ratio between the number of particles entering the second portion and the number of particles leaving the second portion.

Theoretical Guiding

In the following, a theory is presented to help a skilled person in selecting a suspending medium suitable for focusing particles of a given size, and experimental results are reported to support the theory and the workability of some embodiments of the invention.

An aspect of the invention concerns methodology for passive and tunable focusing of particles or cells in dilute suspensions in a flow-through geometry. The methodology is supported by results of microfluidic experiments, which demonstrate how the intrinsic nonlinear elastic forces arising in pressure-driven flows of dilute polymer solutions can be exploited to drive particles away from walls, towards the midplane of the channel in a controllable fashion. We present results of the analytical model to describe the underlying migration mechanism and propose ways for fine-tuning of the transverse particle distribution. Lastly, results of experiments, designed to verify the theoretical predictions, are provided and thoroughly discussed.

In our experiments, we used shallow microfluidic channels of a cross section $h \times w = 45 \times 10^3$ $\mu m^2$ fabricated in microscope cover glasses using photolithography as described in A. Bransky et al., Biosens. Bioelectron. 22, 165 (2006); Microvasc. Res. 73, 7 (2007), incorporated herein by reference (hereinafter: Bransky et al. 2007). A syringe pump (KDS 210, KD Scientific) was used to infuse a dilute (<0.1 vol %) disperse suspension of polystyrene (PS) microspheres (Duke Scientific) through a microchannel inlet at various constant flow rates (at typical velocities of 0.1-1 cm/s). A high-speed CCD camera (CPL MS1000 Canadian Photonic Labs) was mounted on an upright microscope (Nikon 80i). Films of microspheres flowing at the center of the microchannel (at the distance w/2 from the side walls) 20 mm downstream from the inlet at various depths, were recorded directly to a PC, for further analysis by a custom designed image-processing software, as described by Barnsky et al., 2007. The algorithm is capable of counting particles and calculating their velocity in a thin vertical layer of ~1 μm depth.

Figure 5A:
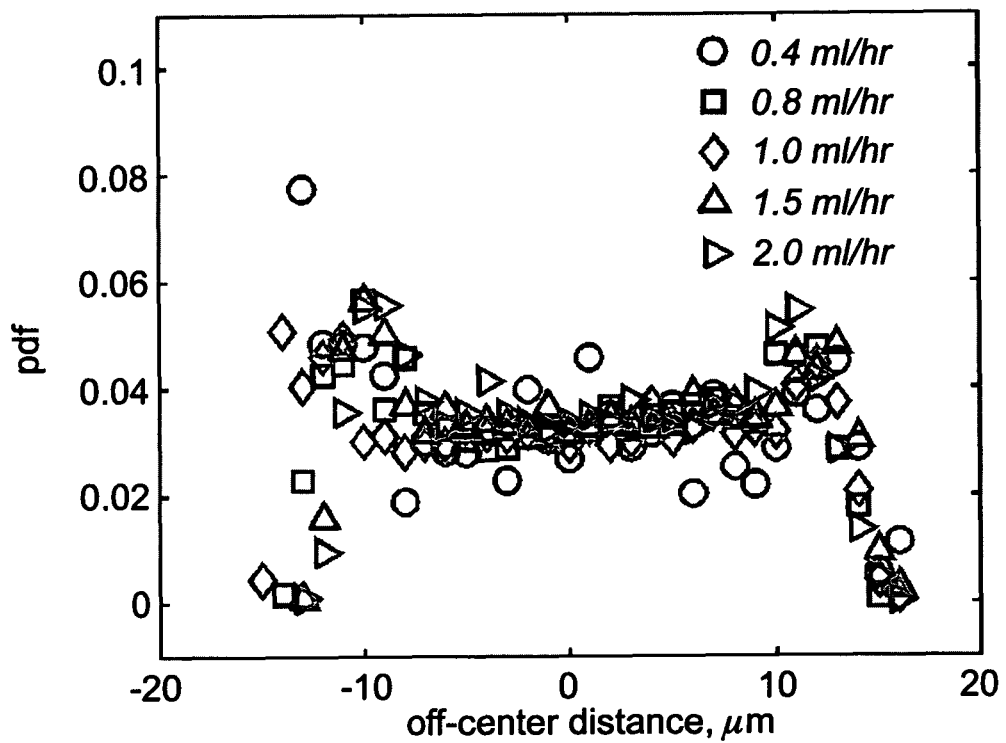
FIG. 5A is a graph showing experimental values of the PDF (particle distribution function) of 8 μm-diameter polystyrene microspheres in glycerol solution vs. the vertical off-center distance. The void symbols are the experimental results.
Figure 5B:
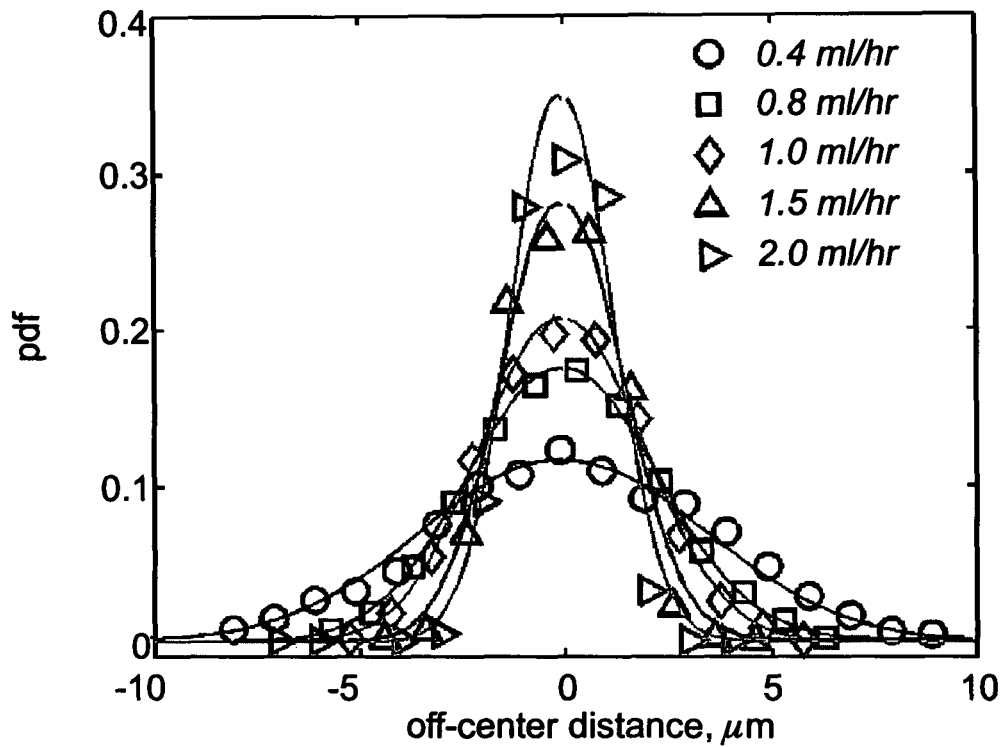
FIG. 5B is a graph showing experimental results obtained in a similar experiment like that described in FIG. 5A, but with polyvinyl pyrrolidone (PVP) solution. The void symbols are the experimental results. The solid lines are Gaussian fits to the experimental results.

We define the particle distribution function (PDF) as the fraction of particles registered in focus at a certain depth, divided by their streamwise velocity and normalized to unity. According to this definition, the PDF must be constant and flow-rate independent, provided that particles follow the streamlines of the ambient flow. We first perform a reference experiment with 8-μm diameter PS microspheres suspended in a viscous Newtonian liquid containing 84 vol % glycerol in deionized water. The solution shear viscosity was measured using a strain-controlled rheometer (ARES, Rheometric Scientific) and was found to be 0.063 Pa·s at 25° C. FIG. 5a represents the experimental PDF vs. the off-center vertical distance upon varying the flow rate. Each point corresponds to a mean value based on hundreds of individual measurements. It is readily seen that particle distribution does not vary with the flow rate and is mostly uniform. We repeat the experiment with PS microspheres suspended in 8 wt % polyvinylpyrrolidone (PVP, MW≈$3.6 \times 10^5$; Sigma-Aldrich) water solution and plot the resulting PDF in FIG. 5b. It is readily seen, that the particles tend to migrate away from the walls and concentrate in the mid-plane, while the focusing intensifies with an increase in flow rate. The previously suggested explanations to particle focusing in the absence of external fields (deformation-induced migration, inertial effects, and shear-induced migration) seem all insufficient for explaining the results shown in FIGS. 5a and 5b. Obviously, deformation-induced migration is not operative for rigid microspheres; inertial effects should yield similar results in both solutions, while shear-induced migration is only observed in concentrated suspensions. Therefore, a novel explanation should be provided.

We shall next demonstrate that the lateral particle migration is driven by the imbalance of the compressive nonlinear elastic forces. These forces in shearing flows are described in terms of the 1st and 2nd normal stress differences, $N_1(\dot\gamma)=\sigma_{xx}-\sigma_{yy}$ and $N_2(\dot\gamma)=\sigma_{yy}-\sigma_{zz}$, respectively (here $\sigma_{ii}$ stands for the diagonal component of the stress tensor, x denotes the direction of the flow, y is the direction of velocity gradient, and z is the vorticity direction). The rigorous analysis of lateral particle migration in plane Poiseuille flow for an analytically tractable case of second-order viscoelastic fluid showed that both $N_1>0$, $N_2<0$ act to drive particles towards the center of the channel (see B. P. Ho and L. G. Leal, J. Fluid Mech. 76, 783 (1976). In order to keep the analysis as general as possible, we construct a simple theory based on scaling arguments. We neglect the $N_2$ contribution and assume the transverse elastic force exerted on the particle is proportional to the variation of $N_1$ over the size of the particle, $F_e \sim a^3 (\partial N_1/\partial y)$ and counterbalanced by the Stokes drag, $F_\eta = 6\pi\eta aV$. Here V is the velocity of lateral migration, a is the radius of the particle, $-d \leq y \leq d$, d is the half-depth of the channel, $\eta$ is the dynamic viscosity that is in general a function of the local shear rate $\dot\gamma$. Equating $F_e$ and $F_\eta$ yields the expression for the lateral migration speed $$V \sim -\frac{a^2}{6\pi\eta}\frac{\partial N_1}{\partial \dot\gamma}\frac{\partial \dot\gamma}{\partial y} \quad (1)$$

For the aspect ratio of $w/h \approx 22$ we approximate the flow by the plane Poiseuille profile. For the power-law fluid, $\eta = m\dot\gamma^{n-1}, \dot\gamma = |du/dy|$ the solution is given by $$u(y) = \frac{1+2n}{1+n}\overline{U}\left[1-\left(\frac{y}{d}\right)^{1+1/n}\right]$$

where $\overline{U}$ is the mean velocity. A power-law behavior, $N_1 = A\dot\gamma^\beta$ ($1<\beta\leq 2$), is expected for dilute solutions of high molecular weight polymers [16]. Thus, substituting $N_1$ and $\dot\gamma$ into (1) we arrive at $$V = C\alpha \overline{U}^\lambda |\zeta|^{(\lambda-n)/n} \quad (2)$$

where $$\alpha = \frac{a^2 \beta A}{6\pi mnd}\left(\frac{1+2n}{nd}\right)^\lambda$$

has the dimensions of $[L/T]^{n-\beta}$, $\lambda = 1+\beta-n$ and $\zeta = y/d$ is the scaled transverse coordinate and C is a constant to be determined later by fitting the model to the experimental data.

Alternatively, the depth-averaged lateral velocity in (2) can be readily found as $$\overline{V} = \delta a^2 W_i \left(\frac{\partial \dot\gamma}{\partial y}\right)_m \quad (2a)$$

where $Wi = N_1/\tau$ is the average Weissenberg number equal to the ratio of elastic stress, $N_1$, and the viscous stress, $\tau = \eta\dot\gamma$, both determined at the mean shear-rate, $$\dot\gamma_m = \frac{(1+2n)}{(1+n)}\frac{\overline{U}}{d}, \left(\frac{\partial\dot\gamma}{\partial y}\right)_m = \frac{1+2n}{n}\frac{\overline{U}}{d^2}$$

and the constant $$\delta = \frac{C\beta}{6\pi\lambda}\left(\frac{1+n}{n}\right)^{\lambda-1}.$$

We further neglect Brownian forces, the hydrodynamic interaction among particles and with the walls, and assume that the streamwise velocity U of the particle is approximately equal to the velocity of the undisturbed flow, u, at its center [18]. Therefore, the trajectory of the particle is the solution of the following equation $$\frac{d\zeta}{d\xi} = \frac{V}{U} = \frac{1+n}{1+2n}\frac{C\alpha\overline{U}^{\lambda-1}|\zeta|^{(\lambda-n)/n}}{1-\zeta^{(n+1)/n}} \quad (3)$$

where $\xi = x/d$ is the scaled axial coordinate. Equation (3) can be readily integrated and the implicit solution is obtained $$F(\zeta,\zeta_0) = C\alpha\overline{U}^{\lambda-1}\xi \quad (4)$$

Figure 6:
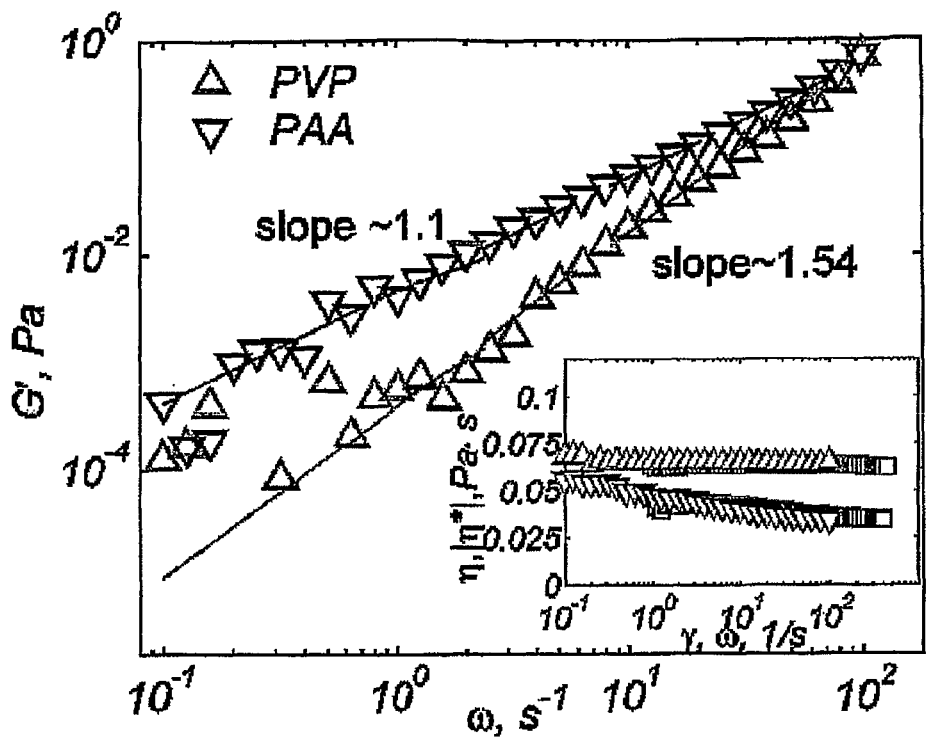
FIG. 6 is a graph showing the rigidity modulus, G', of the polymer solutions PVP (head-up triangles) and PAA (head-down triangles) vs. the oscillatory frequency ω, on a log-log plot. The inset shows the shear viscosity, η (squares), and the complex viscosity, $|\eta^*|(\Delta, \nabla)$, (triangles, as above) of the polymer solutions vs. $\dot\gamma$ and ω, respectively.

Assuming that initially the particle distribution across the channel cross section is uniform, we can estimate the half-width of the central core containing 95% of the particles, $y_{95}$, at the distance from the entrance due to "viscoelastic focusing". Since the envelope of the core is a trajectory, we can compare the experimental results in FIG. 1(b) with the theoretical model based on the solution of (3). The shear viscosity of the PVP solution measured with the ARES rheometer at 25° C. and is found equal to ~0.064 Pa·s. The observed shear-thinning was minor as the viscosity diminishes by less than 3% over the range of shear rates of 0.1-250 s$^{-1}$ (see the inset in FIG. 6) and, therefore, we use n=1 for the PVP solution.

The magnitude of $N_1$ for the PVP solution was too low to be reliably measured in steady shear tests. Instead, we performed the small-amplitude oscillatory shear measurements of the dynamic rigidity ("storage modulus"), G', as a function of the oscillation frequency, $\omega$ (see FIG. 6). Using the rheometric relationship $G'/\omega^2 \sim N_1/2\dot\gamma^2$, that holds between G' and $N_1$ at low values of $\dot\gamma$ and $\omega$, we can estimate the value of $N_1 \approx 0.94\dot\gamma^{1.54}$ mPa. The analogous Cox-Merz relation holds between the shear viscosity, $\eta(\dot\gamma)$, and the absolute value of the complex viscosity $|\eta^*(\omega)|$, as confirmed in the inset in FIG. 6.

Given the rheological properties and the channel dimensions we can calculate a directly and then find the multiplication constant C by fitting the solution of (3) to the experimental data. The values corresponding to $y_{95}$(μm) are calculated from the data shown in FIG. 5b for various flow rates and presented in FIG. 7 as open triangles. The middle curve in FIG. 7 corresponds to the best fit of the theoretical model to the experimental data and there is an excellent agreement between the two. The best fit yields the multiplication constant $C \approx 0.301$.

The scaled width of the PDF due to Brownian forces in a steady state, $2\zeta_B$, can be estimated from the condition, $Pe = aV/D_0 = 1$, where V is given by (2), $D_0$ is the Stokes-Einstein diffusivity of a single particle, and Pe is the Péclet number. For a=0.5 μm and a typical mean velocity of $\overline{U}=1$ cm/s one obtains $\zeta_B \approx 0.004$, so the Brownian transport can be entirely neglected for μm-size particles.

The expression (2) yields $V/\bar{U} \sim \alpha \bar{U}^{\beta-n} V$, where the strength of the focusing is controlled by $\alpha \sim Aa^2/\eta$. The shear thinning (i.e. n<1) may reinforce the focusing. The ratio of depth-averaged migration velocities of shear thinning and Newtonian liquids (with the same elastic properties and zero-shear-rate viscosity) reduces to $$\left(\frac{1+2n}{n}\right)^{1-n} s^{1-n},$$

and for $\bar{U}/d > 1$ s$^{-1}$ this expression is larger than 1 for n<1. Thus, by varying the particle size and altering the elasticity and/or viscosity of the suspending medium one can control the width of the particle distribution at a certain distance downstream. For instance, if the $N_1$ exponent, $\lambda \sim 1$, the particle distribution is expected to be insensitive to the flow rate. To verify the validity of the theoretical prediction, we repeat the experiments using the viscoelastic liquid based on dilute solution of high molecular weight polyacrylamide (PAA), prepared using a solvent of 76 wt % glycerol with 45 ppm PAA (Separan AP30; Dow Chemical Co.). The shear viscosity varies from 0.052 to 0.036 Pa·s over the range of shear rates 0.1-450 s$^{-1}$ and is best approximated by $\eta = 0.047 \dot{\gamma}^{-0.06}$ Pa·s (see the inset in FIG. 6). The dynamic rigidity (G') measurements yield $N_1 = 0.0116 \dot{\gamma}^{1.09}$ Pa (see FIG. 6). The frequency dependence of the dynamic rigidity of a dilute solution of PAA is expected to be $G' \sim \omega^2$, and the deviation of the exponent from the anticipated value of 2, even at the lowest frequencies tested (see FIG. 6), may be due to high polydispersity of the polymer used in the experiments.

Thus, $V/\bar{U} \sim \bar{U}^{0.15}$, and rather weak dependence of the PDF on the flow rate is anticipated. On the other hand, the pre-exponential factor A is about an order of magnitude higher than that measured for the PVP solution, and, therefore, a stronger focusing effect is expected in the PAA solution.

Figure 7:
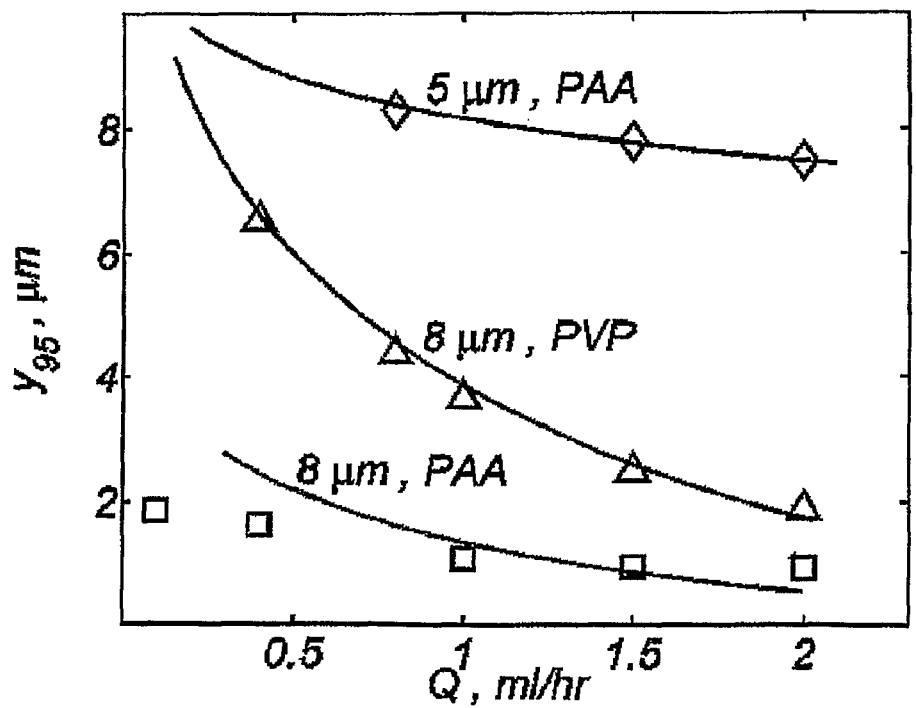
FIG. 7 is a graph showing comparison between the experimental results (void symbols) and the theoretical prediction (solid curves): 8 μm particles, the PVP solution (Δ); 8 μm particles, PAA solution ( ) 5 μm particles, PAA solution (◇). The theoretical curves corresponding to PAA solution have no adjustable parameter.
Figure 8A:
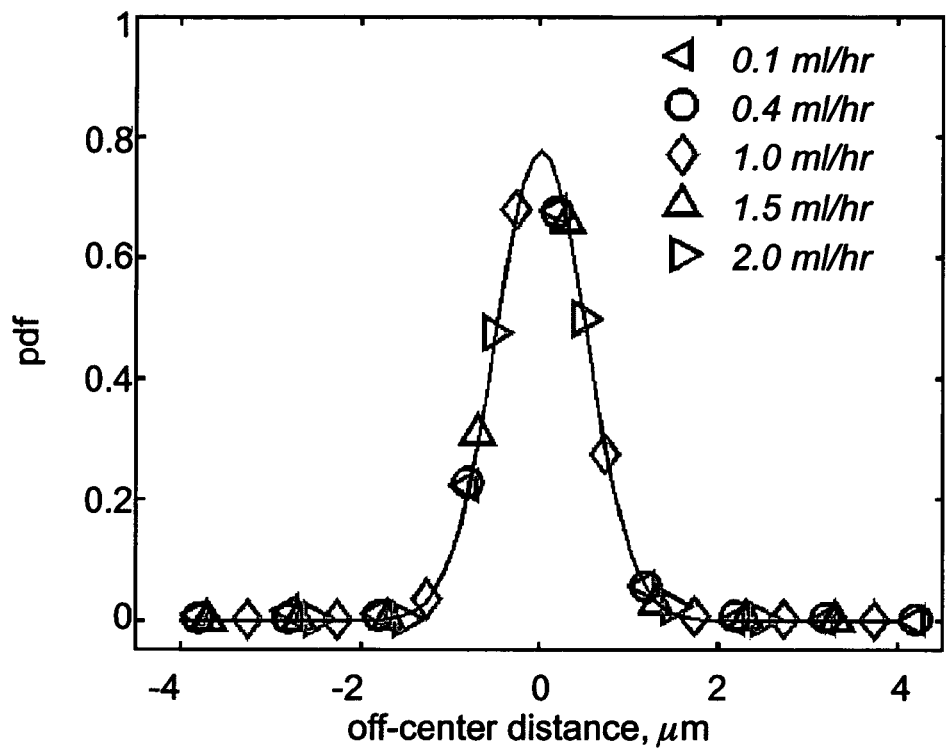
FIGS. 8A and 8B are graphs that show the PDF of the PS microspheres suspended in the PAA solution vs. the vertical off-center position. The void symbols are the experimental results.
Figure 8B:
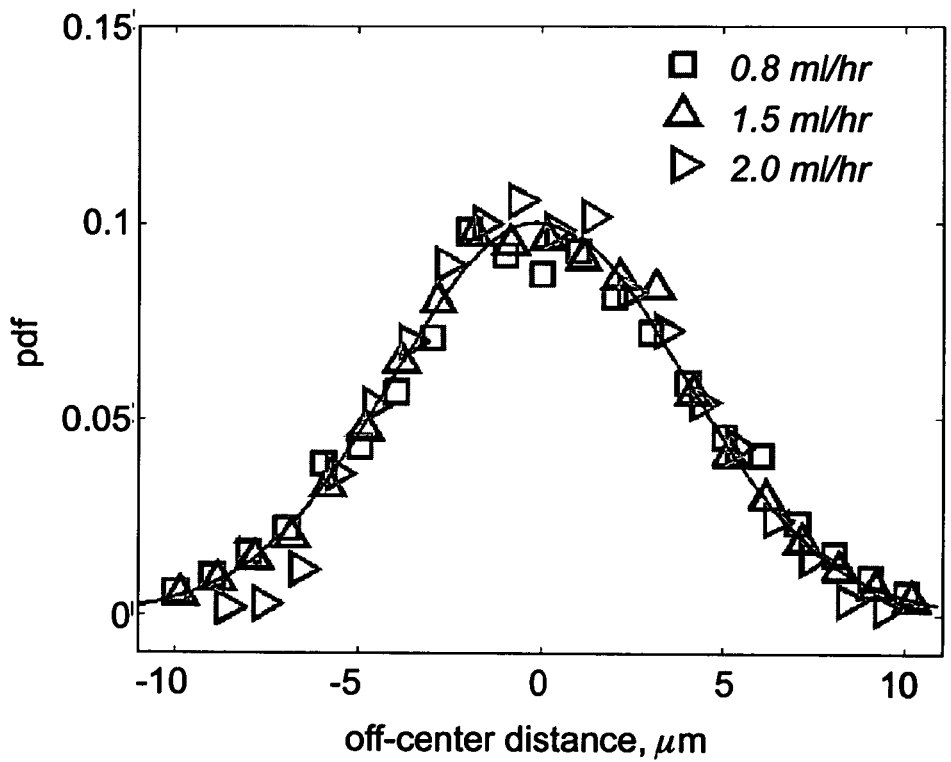

The resultant PDF's of the 8 and 5 μm microspheres are given in FIGS. 8a and 8b, respectively. It can be readily seen that the PDF is almost independent of the flow rate as expected. The particle size effect is evident: the PDF distribution is narrower for larger particles. The corresponding values of $y_{95}$ can be calculated from the PDF's in FIG. 8 and they are depicted in FIG. 7 vs the flow rate for the 5 μm particles (open diamond) and 8 μm particles (open square). The theoretical prediction of $y_{95}$ in the PAA solution [top and bottom curves in FIG. 7] is based on the solution of equation (3) with C=0.301 and does not involve any adjustable parameters. As expected, the focusing effect for 8 μm particles is stronger in the PAA solution than in the PVP solution and the effect of the particle size is considerable. The comparison between the theoretical estimate (without adjustable parameters) and the experimental data shows excellent agreement and validates the hypothesis of the viscoelastic focusing. The agreement between the theoretical prediction and the experiment for 8 μm particles in PAA solution in FIG. 7 is less accurate than that for 5 μm particles, as the experimental resolution in the former case is insufficient: the particles are focused in a very thin layer of less than 4 μm, see FIG. 8(a).

Focusing Prediction Methods

Figure 9A:
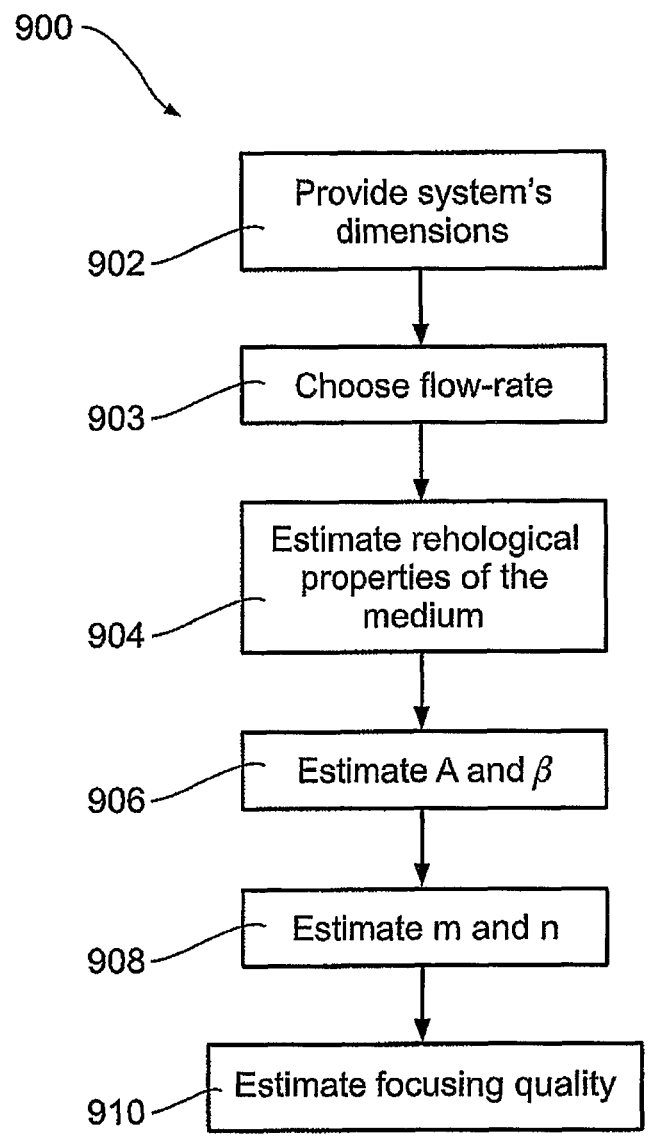
FIG. 9A is a flowchart of actions to be taken in a method 900 of predicting focusing quality of a given suspending medium in a given flow system according to an embodiment of the invention.

FIG. 9A is a flowchart of actions to be taken in a method 900 of predicting focusing quality of a given suspending medium in a given flow system according to an embodiment of the invention.

At action 902, the system's physical dimensions are provided. These dimensions optionally include:

the geometry of the microfluidic channel, including its width w, depth h (or d=h/2 that stands for the channel half-depth), and length between the inlet and the inspection zone; and the estimated size of the particles to be focused.

At 903, a flowrate Q, to be used in the experimental setup is chosen, and the mean stream-wise velocity $\bar{U}$ is estimated from the equation $\bar{U} = Q/A$, where A=h×w.

At 904, rheological properties of the given suspending medium are estimated. The estimated rheological properties optionally include: dynamic viscosity, $\eta$ (Pa·s), as a function of shear rate, $\dot{\gamma}$; and elastic modulus G'(Pa) as a function of the oscillatory frequency, $\omega$. Optionally, these estimations are based on data available in the literature. Optionally, these data are collected experimentally, for instance, with a commercially available rheometer.

At 906, the constants A and β in the equation $N_1 = A\dot{\gamma}^\beta$ are estimated.

Optionally, this estimation is based on the measurements taken at 904, with the rheometric equality $N_1 \approx 2G'$.

If $N_1$ is large enough to be directly measured by an a commercially available rheometer (typically, in the order of tens of Pa) $N_1$ is optionally measured directly.

At 908, the parameters m and n in the equation $\eta = m\dot{\gamma}^{n-1}$ are estimated. This estimation is optionally based on data available in the literature. Alternatively, the estimation comprises fitting measured rheological properties to the above equation.

At 910 focusing quality is estimated by solving equation 4 above using the data provided at action 902 and 903 and the estimations obtained in actions 904-908. Optionally, the focusing quality is estimated by the dimensionless position $\zeta = y/d$ of a test particle. For example, if one wants to know what percent of the particles will be vertically focused within the central layer of depth 4 μm in the microchannel with half-depth of d=40 μm at a distance of 20 mm from the inlet in the streamwise direction, Eq. (4) should be solved for $\zeta_0$ with $\zeta = 4/40 = 0.1$ and $\xi = 2000/40 = 50$. For example, the resulting value of $\zeta_0 = 0.75$ means that approximately 75% of the particles will be focused within the central core of depth 4 μm at the distance of 20 mm downstream from the inlet.

Many dilute solutions of monodispersed linear polymers, exhibit particular well-characterized rheological behavior (known in the art as Boger liquids): according to which, $n \approx \text{const}$, $N_1 = A\dot{\gamma}^2$.

The term "monodispersed polymers" is used, in this context, to denote polymers with narrow distribution of molecular weights. Examples of linear polymers that in dilute solutions provide Boger-liquid behavior include monodispersed polyacrylamide and polyethyleneglycol.

In the case of Boger liquids n=1 and β=2 and the estimate of the focusing quality considerably simplifies. A flowchart of such simplified method (900') is provided in FIG. 9b.

Figure 9B:
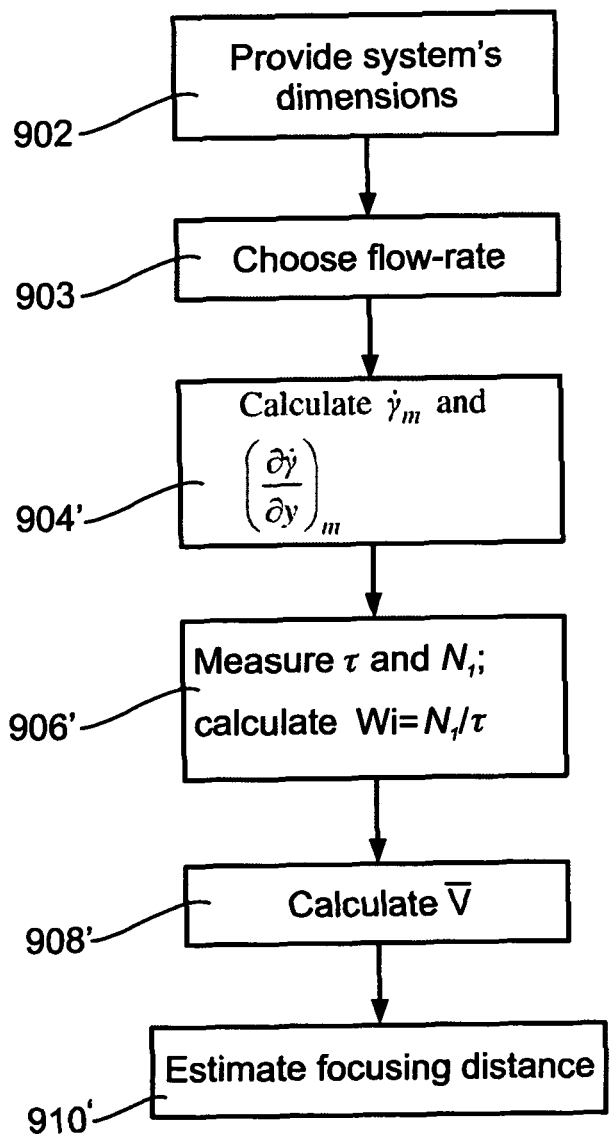
FIG. 9B is a flowchart of actions to be taken in a simplified method 900' of predicting focusing quality of a given suspending medium in a given flow system according to an embodiment of the invention.

FIG. 9B is a flowchart of actions to be taken in a method 900 of predicting focusing quality of a given suspending medium in a given flow system according to an embodiment of the invention.

Actions 902 and 903 in FIG. 9b are just like the same actions in FIG. 9a.

At 904', the mean shear-rate and the mean gradient of the shear-rate are calculated from the formulae: $\dot{\gamma}_m = 3\bar{U}/2d$ and $(\partial \dot{\gamma}/\partial y)_m = 3\bar{U}/d^2$ from the values provided at actions 902 and 903.

At 906' values of the viscous stress τ and the normal stress $N_1$ are measured, and $Wi = N_1/\tau$ is calculated. Measurements of τ and $N_1$ optionally are carried out with a commercial rheometer. These values are optionally measured only at one shear-rate, which is equal to $\dot{\gamma}_m$ as was calculated 904'.

Accurate normal stress measurements are usually not available via commercial rheometers, therefore the normal stress is optionally estimated from the elastic modulus G' measured in oscillatory shear measurements using commercial rheometer at the single frequency $\omega=\dot{\gamma}_m$ and using the relation $N_1 \approx 2G'$ to obtain from the measured data the normal stress.

At 908', Weissenberg Number $Wi=N_1/\tau$ is calculated using the data obtained at 906'.

At 908', the mean lateral velocity of the particles $\bar{V}$ is calculated based on the quantities calculated at 904-908 and Eq. (2a) and the input that for Boger liquids $\delta \approx 0.6/6\pi$.

At 910' the streamwise distance at which particles will be fully focused to the central horizontal plane of the channel is estimated as $l \sim (\bar{U}/\bar{V})d$.

General Comments

It is expected that during the life of a patent maturing from this application many relevant suspending mediums, flow cytometers, and FACS machines will be developed and the scope of the term corresponding terms is intended to include all such new technologies a priori.

The terms "comprises", "comprising", "includes", "including", "having" and their conjugates mean "including but not limited to".

The term "exemplary" means "serving as an example, instance, or illustration".

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of focusing particles, the method comprising:
    providing a suspension of the particles in a first suspending medium; and
    flowing the suspension in a channel having a longitudinal axis and a cross-section perpendicular thereto and having at least one cross-sectional dimension smaller than 100 µm,
    wherein the first suspending medium has viscoelastic properties such that flowing the suspension in the channel focuses a concentration of the particles in a focus region including a center of the channel, and wherein the concentration of the particles is maximum at the center of the channel.

2. A method according to claim 1, wherein said focus region is aligned with the longitudinal axis of the channel.

3. A method according to claim 1, wherein a first dimension of the cross-section is smaller than about 100 µm and a second dimension of the cross-section orthogonal to the first dimension is sufficiently larger than the first dimension, such that the particles suspended in the first suspending medium flow in a substantially single-particle layer in the focus region.

4. A method according to claim 1, wherein a first dimension of the cross-section and a second dimension of the cross-section orthogonal to the first dimension are of substantially a same size no greater than about 100 µm, such that the particles suspended in the first suspending medium are caused to flow in a substantially single-file focus region.

5. A method according to claim 1, wherein:
    said suspension comprises particles of a first size and a second size larger than the first size; and
    said viscoelastic properties are such that flowing the suspension in the channel preferentially directs particles of the second size towards the focus region.

6. A method according to claim 1, wherein providing a suspension further comprises:
    obtaining a suspension of the particles in a second suspending medium; and
    adding said second suspending medium with said first suspending medium.

7. A method according to claim 1, wherein providing a suspension further comprises:
    providing a plurality of suspending media having various viscoelastic properties;
    selecting said first suspending medium from said plurality of suspending media responsive to the viscoelastic properties of the media; and
    suspending the particles in the selected suspending medium.

8. A method according to claim 7, wherein selecting comprises selecting responsive to the size of the particles.

9. A method according to claim 1, further comprising adding a high molecular weight polymer to the suspension to increase elasticity of the first suspending medium.

10. A method according to claim 1, wherein the particles are cells.

11. A method according to claim 1, wherein providing a suspension of particles in a first suspending medium includes diluting blood with the first suspending medium.

12. A method according to claim 1, wherein the channel has a length of at least 1 mm.

13. A method according to claim 1, wherein the first suspending medium is formulated of materials having elasticity and shear thinning properties such that the particles concentrate in the focus region substantially independent of a flow rate of the particles.

14. A method according to claim 1, wherein the first suspending medium is a shear thinning fluid.

15. A method according to claim 1, wherein in the focus region, centers of about 95% of the particles are focused in a layer of less than about 4 µm.

16. A method according to claim 1, wherein flowing the suspension occurs in a manner causing particles to flow in a substantially single-particle layer in the center of the channel.

17. A method according to claim 1, wherein flowing the suspension occurs in a manner causing particles to flow in a multi-particle layer in the center of the channel.

18. A method according to claim 1, wherein flowing the suspension occurs in a manner causing centers of at least 90% of the particles to locate in a layer having a thickness of less than half the height of the channel.

19. A method according to claim 1, wherein flowing the suspension occurs in a manner causing centers of about 95% of the particles to concentrate in a layer of about 2 μm thick at a distance of at least about 20 mm from a channel inlet.

20. A method according to claim 1, wherein flowing the suspension occurs in a manner causing particles to be driven away from channel walls, toward a mid-plane of the channel.

21. A method according to claim 1, wherein flowing the suspension occurs in a manner causing the particles to be focused in a central horizontal plane of the channel.

22. A method according to claim 9, wherein the high molecular weight polymer includes a high molecular weight polyacrylamide (PAA).

* * * * *